US005725482A

United States Patent [19]
Bishop

[11] Patent Number: 5,725,482
[45] Date of Patent: Mar. 10, 1998

[54] METHOD FOR APPLYING HIGH-INTENSITY ULTRASONIC WAVES TO A TARGET VOLUME WITHIN A HUMAN OR ANIMAL BODY

[76] Inventor: Richard P. Bishop, P.O. Box 10495, Burke, Va. 22009

[21] Appl. No.: 599,297

[22] Filed: Feb. 9, 1996

[51] Int. Cl.[6] ................................ A61B 17/022
[52] U.S. Cl. .................... 601/2; 128/660.03; 607/2
[58] Field of Search .................. 128/653.1, 660.03; 601/2, 4; 607/2; 73/628, 632; 204/157.15; 367/153

[56] References Cited

U.S. PATENT DOCUMENTS

| | | |
|---|---|---|
| 5,357,757 | 10/1994 | Lucas . |
| 5,367,139 | 11/1994 | Bennett et al. . |
| 5,437,178 | 8/1995 | Esin et al. . |
| 5,503,150 | 4/1996 | Evans . |
| 5,524,620 | 6/1996 | Rosenschein . |
| 5,535,627 | 7/1996 | Swanson et al. . |
| 5,540,737 | 7/1996 | Fenn . |
| 5,569,854 | 10/1996 | Ishida et al. . |
| 5,582,578 | 12/1996 | Zhong et al. . |
| 5,613,940 | 3/1997 | Romano . |

Primary Examiner—Marvin M. Lateef
Assistant Examiner—Shawna J. Shaw
Attorney, Agent, or Firm—Stephen E. Clark

[57] ABSTRACT

A method for focussing vibrational energy upon a target volume within a surrounding contiguous medium imparts high intensity energy upon the target volume from low level energy sources. A plurality of standing compression waves are established within the medium along corresponding longitudinal axes between opposing pairs of coordinated transducers. The target volume is located at the common intersection of the axes of the standing compression waves. Opposing pairs of transducers are positioned from each other at a distance equal to an integer multiple of half wavelengths of the corresponding standing wave therebetween. The phase angle of each standing compression wave is regulated so as to cause each wave to be at its maximum intensity (amplitude) within the target volume at the point of common intersection with the other standing waves. The plurality of intersecting standing waves constructively interfere within the target volume, thereby imparting more intense vibrational energy upon the target volume that upon the surrounding medium.

13 Claims, 4 Drawing Sheets

METHOD FOR APPLYING HIGH-INTENSITY ULTRASONIC WAVES TO A TARGET VOLUME WITHIN A HUMAN OR ANIMAL BODY

BACKGROUND OF THE INVENTION

1. Field of Invention

The present invention relates to a method and apparatus for therapeutically focusing sonic or ultrasonic waves within a finite volume within an insonified medium. More particularly, the present invention relates to a method and apparatus for generating a plurality of standing waves which constructively intersect within a volume of target tissue within a human (or animal) body.

2. Description of the Prior Art

There are numerous known medical applications for which relatively high intensity sonic or ultrasonic waves may be advantageously used to induce various desired effects on the human (or other animal) body. Sonic and/or ultrasonic waves may be used, for example, to disrupt tissue and other materials, such as to break up kidney stones, blood clots or respiratory congestions. Sonic and/or ultrasonic waves may also be used to heat cancerous growths so as to make ionizing radiation treatment more effective. In addition, low-intensity sonic wave application is believed to facilitate healing.

Prior methods of introducing sonic and/or ultrasonic waves for medical treatment of the human body typically involve either applying the waves to the entire body, for example by immersing the body in an ultrasonic bath, or by localized vibration via a catheter, probe or similar instrument.

There are several problems associated with prior methods and apparatus of applying sonic and/or ultrasonic waves to the human body. When vibrational waves are applied, for example, through a catheter, the character of the applied vibrations (i.e. the location, the intensity, interaction with the vibrating medium, etc.) is limited due to the inherently small size of the catheter, or by the location of the blood vessel into which the catheter is to be inserted.

Also, because some prior means of applying sonic waves to the human body for medical treatment involve making an incision through, against or into which a vibrating member must be inserted, access may be limited by the damaged region in the vicinity of the incision, and there is an increased risk of infection associated with such methods.

Another problem with prior means of applying sonic waves to the human body for medical treatment is the collateral damage or effect that the waves may cause to areas of the body adjacent to or beyond the intended target tissue.

A problem associated with prior means of applying sonic waves to the human body for medical treatment involving vibrating probe members is that, because such probes are typically very small, the amount of power which can be applied with the probe is correspondingly limited. In addition, such probes also may directly damage areas of the body surrounding the target tissue.

As will be described more fully hereinbelow, an apparatus constructed in accordance with the present invention establishes a plurality of standing sonic waves within a patient's body to produce a therapeutic effect upon a target volume of tissue. Prior methods and apparatus for generating standing waves in media typically employ a single vibrator mechanism which imparts a coherent wave into a medium. The wave thus produced propagates through the medium until it encounters a substantially stationary reflective surface off of which the wave bounces directly back toward its source. A standing wave may be produced in this manner by adjusting the distance between the vibration source and the reflective surface to an integer multiple of the wavelength of the vibration. A problem with such transmitter-reflector methods of establishing standing waves is that the (single) transmitter has to emit vibrations of high enough intensity and of high enough quality to travel all the way from the emitter to the reflector and then back to the emitter.

SUMMARY OF THE INVENTION

Accordingly, it is a primary object of the present invention to provide a method and apparatus for applying sonic or ultrasonic waves to a target volume of tissue inside of a human (or other animal) body by producing multiple individual standing waves within the body, and regulating the constructive intersection of said waves within said target volume.

It is another object of the present invention to provide a method and apparatus of the character described wherein the coordinated constructive intersection of said waves within a target volume causes said target volume to incur vibrational intensity greater than the vibrational intensity of any of the individual standing waves, and wherein the target volume of tissue incurs vibrational intensity greater than that which is incurred outside of the target volume.

It is another object of the present invention to provide a method and apparatus of the character described wherein each of said multiple standing waves is generated by opposing pairs of sonic transducers which cause a standing wave to set up inside of the body between the two transducers.

It is another object of the present invention to provide a method and apparatus of the character described in which the location of the intersection of said multiple standing waves may be user-adjusted to effect target volumes at various locations and of various sizes within the body.

It is another object of the present invention to provide a method and apparatus of the character described in which the intensity of said coordinated constructive intersection of said waves may be user-regulated, and in which relatively high power levels may be focused upon selected target volumes without adversely affecting surround regions of the body.

It is another object of the present invention to provide a method and apparatus of the character described which does not require an incision into the body, thereby reducing the risk of infection to the patient.

It is another objective to provide a modification of the present invention wherein a target volume inside of a medium is subjected to non-standing coherent sonic waves which constructively intersect within the target volume such that the target volume incurs vibrational intensity greater than that which is incurred outside of the target volume.

Further objects and advantages of my invention will become apparent from a consideration of the drawings and ensuing description thereof.

DESCRIPTION OF THE PREFERRED EMBODIMENT

The preferred embodiment of the present invention is an apparatus and method by which sonic waves are applied to a target volume 30 of tissue within a human (or other animal) body member 20 in order to therapeutically affect the target volume 30 of tissue without adversely affecting surrounding regions of the body member 20. As used herein, "sonic waves" refers to physical vibrations which propagate through a given medium at a speed of sound which is characteristic of said medium, regardless of whether or not such waves are at a frequency or intensity which is audible.

Figure 2:
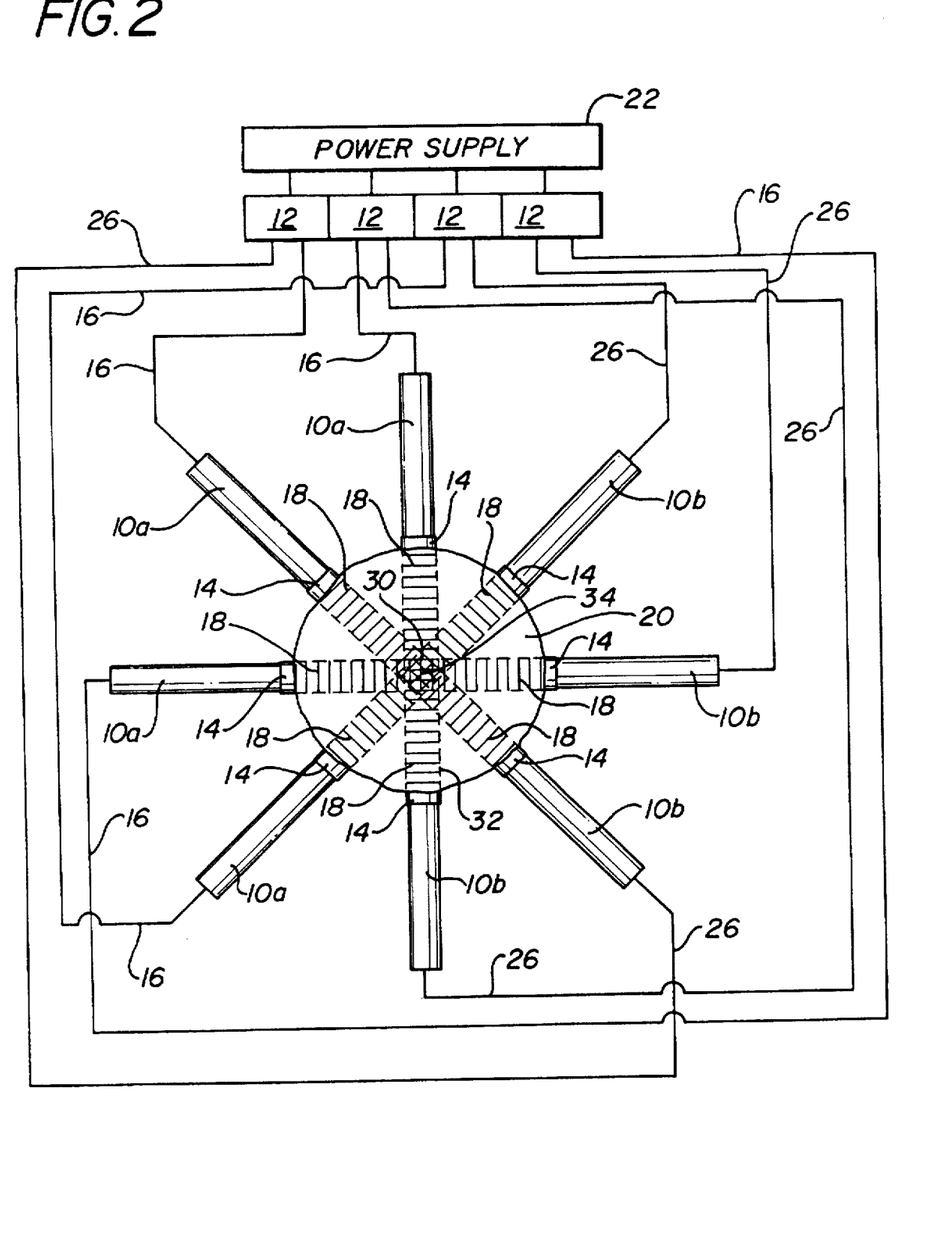
FIG. 2 is a schematic view illustrating a plurality of pairs of opposing transducers used to generate intersecting standing waves within a target volume in accordance with the present invention.

The invention accomplishes the described effect by producing a plurality of therapeutically benign standing sonic waves 18 within the body member 20, as indicated in FIG. 2. The "therapeutically benign" waves 18 are preferably at such low intensity levels that individual waves 18 have no substantive effect on the body member 20. The frequency and phase angle of the various individual standing waves 18 are regulated by a computer 12 so as to cause the plurality of waves 18 to constructively intersect within a selected target volume 30 within the patient's body member 20.

Figure 1:
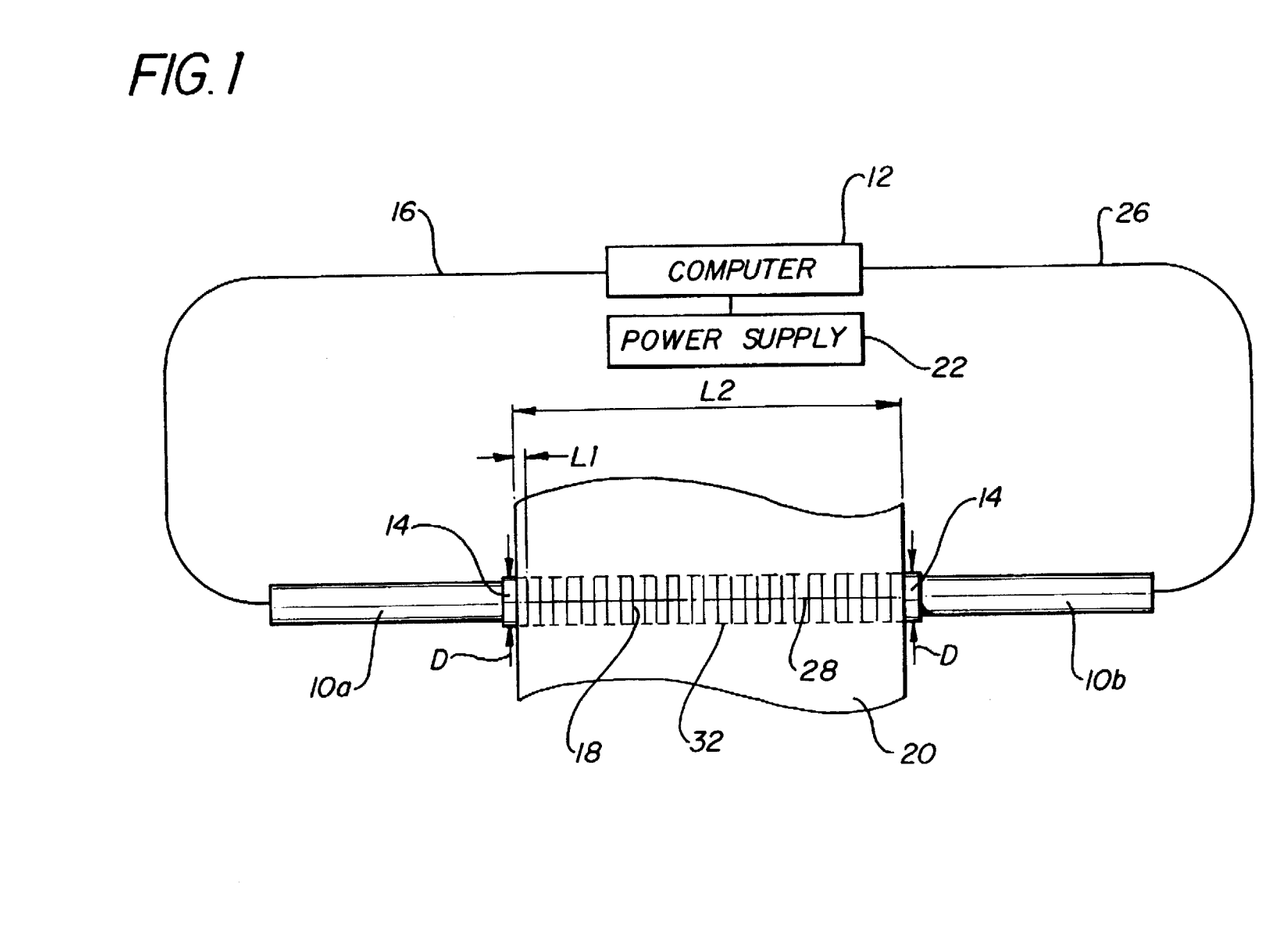
FIG. 1 is a schematic view illustrating a pair of opposing transducers used to generate a standing wave in accordance with the present invention.

Referring to FIG. 1, each standing wave 18 is produced by a pair of diametrically opposing transducers 10a and 10b. Each transducer (10a and 10b) preferably comprises a flat circular vibrating surface 14 which may be operationally placed adjacent the outer surface of the patient's body member 20 and aligned with each other along an axis 28. In the preferred embodiment of the invention, each transducer of a transducer pair (10a and 10b) produces waves of identical frequency and amplitude in the body member 20. In the preferred embodiment of the invention opposing pairs of circular vibrating surfaces 14 are of equal diameter D. The transducers 10a and 10b of a given transducer pair are in electrical communication with the computer 12 via electrical conductors 16 and 26, respectively. The computer 12 is connected to a power supply 22.

In order to establish a standing wave between opposing transducers (or more particularly, between opposing vibrating surfaces 14), the distance L2 between facing vibrating surfaces 14 must be an integer number of half wavelengths such that there occurs an antinode of the standing wave 18 at each of the vibrating surfaces 14.

As used herein, "transducer" or "transducers" refers to any device by means of which the energy of one power system may be transmitted to another system (whether of the same type or not); or, more particularly, any device by means of which electrical energy is converted to mechanical vibrational energy which may subsequently be transmitted to another system (i.e. to the patient's body member 20). In the preferred embodiment of the invention, the transducer 10 comprises a magnetostrictive element which is capable of changing in physical size and/or shape responsive to electrical signals (via electrical conductors 16 or 26) supplied to the transducer from an external electrical power supply 22. Transducers 10 comprising magnetostrictive elements may be advantageously used in accordance with the present invention to produce controlled vibrations in the frequency range of 150 Hz to 25 KHz; while piezo-electric transducer elements may be advantageously used to produce vibrations in a higher frequency range (e.g. 20 KHz to 20 MHz). Transducers comprising other electrical-to-mechanical conversion means may alternatively be used in accordance with the present invention.

In the preferred embodiment of the invention the vibrating surfaces 14 of opposing pairs of transducers 10a and 10b oscillate back and forth in a direction of motion parallel to the longitudinal axis 28 between the respective transducers. It will be understood that the patient's body member 20 provides a medium through which vibrational energy will propagate away from a vibrational energy source (i.e. vibrating surface 14) in accordance with the nature of the vibration, the character of the vibrating surface 14, and the local speed of sound of the medium (i.e. the patient's body member 20). In the preferred embodiment of the invention the vibrating surface 14 is oscillated at a frequency sufficient to generate a substantially cylindrical compression wave having substantially planar wave fronts, the axis of which cylinder (generally designated 32 in the figures) corresponds to the longitudinal axis 28 between the corresponding transducer pair 10a and 10b. In order to generate a substantially cylindrical planar compression wave 18, the wave length L1 of the wave being generated should be substantially smaller than the diameter D of the vibrating surface 14. In the preferred embodiment of the invention, in order to generate cylindrical planar compression waves of high resolution, the diameter D of the vibrating surface 14 is at least four times as great as the wave length L1 of the compression wave 18 produced by the oscillation of the vibrating surface 14. This relationship between the wavelength L1 of the wave being generated and the diameter D of the vibrating surface 14 may be mathematically expressed by the equation $$L1 \ll D. \tag{1}$$

The wavelength L1 may be mathematically expressed by the equation $$L1 = V/f, \tag{2}$$

where V is the speed of sound and f is frequency of the sound wave.

Thus, equation (1) may be rewritten as $$L1 \ll D$$

$$v/f \ll D \tag{3}$$

$$V/D \ll f. \tag{4}$$

Accordingly, as will be appreciated by one skilled in the art, it is evident that this relationship inherently implies that the frequency of the wave being generated should be greater than the local speed of sound in the medium divided by the diameter D of the vibrating surface 14.

In media of interest for practicing the preferred embodiment of the invention, (i.e. in human body members 20) the speed of sound is typically around 5000 feet per second (60,000 inches per second). Accordingly, a compression wave 18 having a frequency of, for example, 500 KHz (500,000 cycles per second) in such media would have a wave length of approximately 0.12 inches; and the diameter D of the vibrating surface 14 would preferably be at least four times the wave length, or at least 0.48 inches.

The wave 18 produced by the opposing transducers (10a and 10b) is a standing compression (longitudinal) wave 18, resulting from the superposition of two similar plane waves of identical frequency and amplitude, travelling in opposite directions. Because the diameter D of the vibrating surface 14 is large relative to the wave length L1 of the wave produced, the oscillations generate an ultrasonic "beam" that is unidirectional with substantially planar wave fronts; but the lateral extent (e.g. corresponding to the diameter of cylinder 32) of the "beam" remains substantially the same as the diameter of the vibrating surface 14.

It will be appreciated that standing cylindrical compression waves (for example wave 18) have two unique properties which contribute markedly to their usefulness for this invention. First, they are not attenuated with distance to the degree that spherical waves are, as they exhibit little spherical spreading. Second, their extent is limited to the cylindrical space 32 generated between the circular vibrating surfaces 14 of the opposing transducers 10a and 10b, so they do not "leak" sound out into surrounding regions of the patient's body member. Accordingly, multiple "beams" (or vibration waves) can be produced that do not interact except in the limited volume of space desired, (i.e. within the target volume 30 defined by the intersection of the cylindrical spaces 32 between corresponding pairs of circular vibrating surfaces 14).

Referring now to FIG. 2: When multiple standing waves 18 are caused to intersect within a single target volume 30 defined by the intersection of the cylindrical spaces 32 between corresponding pairs of circular vibrating surfaces 14, and the axes of all of the cylindrical spaces 32 intersect at the same point (i.e. within the target volume 30), and the various standing waves 18 are in phase at that point (i.e. within the target volume 30), the intensity of the sound is much greater at that point (and only that point) than at any other point. The sound intensity throughout the rest of the insonified space (e.g. the rest of the patient's body member 20) can be completely benign while the intensity at the point of intersection (i.e. inside the target volume 30) can be the strength required to produce the desired effect.

Ultrasonic waves interact with matter in various ways, depending upon the nature (i.e. frequency, duration, amplitude, etc.) of the waves and depending upon the nature (i.e. physical, chemical, and biological properties, etc.) of the interacted matter. Three mechanisms by which ultrasound interacts with matter have been identified: mechanical, thermal, and cavitation. All three of these mechanisms can cause "damage" to biological tissue. Although in the preferred embodiment of the invention sonic waves are focused upon a target volume of biological tissue in order to produce a desired effect upon certain matter within the target volume, it will be understood that the present invention may also be employed to focus sonic waves in non-biologic applications. Furthermore, although the present disclosure describes the preferred application of the present invention wherein sonic waves are focused upon a target volume of biological tissue in order to "damage" certain constituent elements of the tissue (for example, to kill harmful viruses), the described effect upon the tissue is understood to be both desirable, advantageous and controllable.

The first mechanism by which damage can be induced by ultrasonic interaction is mechanical. Mechanical interactions generally include all but thermal and cavitational effects. The ultrasonic wave is propagated through the medium by interactions between neighboring particles, causing the particles to undergo considerable changes in velocity and acceleration. A discrete body (e.g. a virus) with a different density than that of the surrounding medium (e.g. blood) experiences a force in the ultrasonic field because acoustic pressure is applied over the surface of the object. This force causes translational motion or rotational motion of the object. The translational motion may transport biologic particles (e.g. cells) to highly localized regions within the ultrasonic field. In addition, rotary motion may give rise to acoustic streaming (circulatory flow of the fluid) and spinning of intracellular particles. At high intensities, high-velocity gradients are formed near solid boundaries. The resulting microstreaming (i.e. rapid movement of fluid in a localized area) can fragment the macro-molecules situated in these regions.

The second mechanism by which damage can be induced is thermal. As the ultrasonic beam (e.g. standing wave 18) travels through the medium, the intensity decreases as the sonic energy is absorbed and converted into heat. The increased temperature has the potential to cause irreversible tissue damage. The rate of temperature rise depends on the temporal average intensity, the absorption coefficient of the medium, the cross-sectional area of the beam, the duration of exposure, and the heat-transport processes (thermal conductivity and blood flow). Within the frequency range of 1 to 10 MHz, the absorption coefficient increases with frequency.

The third mechanism by which damage can be induced is cavitation. As the ultrasound wave propagates through the medium, regions of compression and rarefaction are created. Thus, localized regions in the medium are subjected to increases and decreases in pressure in an alternating fashion. These pressure changes can cause gas bubbles to form and grow and to exhibit dynamic behavior. This phenomenon is known as cavitation. In stable cavitation, microbubbles already present in the medium expand and contract during each cycle in response to the applied pressure oscillations. The bubble may also grow in size as dissolved gas leaves the solution during the negative-pressure phase. At a characteristic frequency, which is a function of the size of the bubble, the vibration amplitude of neighboring liquid particles is maximized. This condition is called volume resonance. Oscillations of the gas bubble may produce high shearing forces in the nearby surrounding areas. Stable cavitation may also give rise to microstreaming. The radial oscillatory motion of the gas bubble is not always spherically symmetric. An adjoining solid boundary may distort the motion of the bubble, causing eddying motion near the air-liquid interface. High velocity gradients are created in the localized region of the oscillatory boundary layer, and biomolecules or membranes subject to the high velocity gradients can fragment or rupture.

Transient cavitation is a more violent form of cavitation. The changing pressure during the compression phase causes the bubbles to collapse completely, producing highly localized (within 1 micrometer) shock waves. In addition, very high temperatures (up to 10,000 deg. K) and pressures (100 megapascals or higher) are created within the bubbles, resulting in the decomposition of water into free radicals. These pressures and temperature changes may also drive chemical reactions.

The intensity of interest in the preferred embodiment of the present invention is that which develops "transient cavitation" within the target volume 30. Typical intensities have been reported in the range of 1 to 10 watts/square centimeter, while intensities less than 1 watt/square centimeter are, in most cases, completely benign when applied for less than 100 seconds. Accordingly, from 3 to 10 such intersecting standing waves 18 may be sufficient to accomplish the desired effect upon a target volume 30 of tissue in a manner which is completely safe to tissue outside of the target volume 30. Although 3 to 10 such intersecting standing waves 18 are employed in the preferred embodiment of the invention, it should be understood that the present invention contemplates any number of intersecting standing waves in which the intensity of the intersecting waves at the point of intersection is greater than the maximum intensity of any single standing wave.

To generate intersecting standing waves 18, two parameters must be controlled. First, the distance between the opposing transducers 10a and 10b (or more particularly, between facing vibrating surfaces 14) must be an integral number of wavelengths. This is readily accomplished, since the frequency of interest will generally not change during any specific procedure. Second, the point of intersection (i.e. the target volume 30) must be located at an antinode, a point corresponding to a peak in the standing wave intensity. This may be accomplished by physically moving the transducer pairs (10a and 10b) in concert, and is preferably accomplished with some means to ensure that all of the intersecting "beams" (i.e. standing waves 18) are at a peak intensity at the same point in space and time. Several methods by which this can be accomplished are described below.

One means of ensuring that all of the intersecting "beams" (i.e. standing waves 18) are at a peak intensity at the same point in time and space is to place a sensor (not shown) at the point of interest, i.e. within the target volume 30. The intensity level of each individual standing wave can be detected by the sensor. The corresponding transducer pair (10a and 10b) may then be longitudinally moved until the sensed intensity level at the sensor is at a maximum. This procedure is then repeated for each transducer pair.

Alternatively, remote imaging such as ultrasonic imaging can be used to observe the oscillations at the target volume 30. Another means of ensuring that all of the intersecting "beams" (i.e. standing waves 18) are at a sufficiently high intensity at the same point in time and space is to rapidly move the "beams", (or more specifically, longitudinally move corresponding transducer pairs (10a and 10b), in a coordinated pattern so that, at some time in the procedure, the required intensity is obtained.

Alternatively, the speed of sound transmission through several layers of tissue, bone and liquid may be known or calculated in advance, so that the required transducer positions can be predetermined too. This approach may be combined, with potentially great effectiveness, by using the information obtained through reaching the standing wave condition for each transducer pair 10a and 10b. The requisite transducer spacing will vary with the speed of sound in the intervening media, since the spacing must be an integral number of wavelengths. Foreknowledge of the speed of sound in various media can be combined with knowledge of the approximate thicknesses and nature of the media to arrive at a very accurate picture of the sound transmission conditions. This latter approach is preferred, since the whole system will be controlled with a computer 12 capable of performing the needed calculations.

It will be understood from the above disclosure that the present invention may be practiced by causing the antinodes of a plurality of intersecting standing pressure waves to constructively interfere with each other at the common point of intersection of the respective standing pressure waves. Accordingly, it will be understood that, in the preferred embodiment of the invention, the size of the target volume 30 which may be directly affected at any given instant corresponds to the volume within the intersecting cylindrical 32 "sound beams" which is instantaneously occupied by antinodes of the respective standing pressure waves 18. Thus, in the preferred embodiment of the invention, the length of the target volume 30 along the longitudinal axis 28 of any given standing wave 18 is approximately one-half wave length, (i.e. within ¼ wavelength of the antinode of the respective standing wave).

As described above, in the preferred embodiment of the invention, the length of the target volume 30 along the longitudinal axis 28 of any given standing wave 18 is approximately one-half wave length, (i.e. within ¼ wavelength of the antinode of the respective standing wave). However, it will be understood that by moving each of the various transducer pairs (10a and 10b) in concert so as to move the point of intersection 34 of the of their respective longitudinal axes 28, the volume affected by the combined vibrational energy of the standing waves can be varied (i.e. increased) over time.

This invention has numerous applications in the medical, as well as other non-medical, fields. Such applications include, but are not limited to:

Acceleration of the rate of dewatering of plastic concrete, so as to speed up the onset of curing of the concrete, and so as to enhance the strength and uniformity of the concrete;

De-foaming and de-gassing, including defoaming of beverages;

Fluidization of materials, including granules and powders, for conveyance;

Cleaning and sterilization by sonically activating enzymes;

Deaggragation, dispersion and/or reduction of particle size in the target volume;

Crystallization and/or precipitation of materials, including filtering particulates from liquids and gases, for example by causing particulates to accumulate and coalesce within the nodes of standing waves;

Welding of materials heated by focused sonic energy;

Consolidation of food mixtures to reduce water content;

Acceleration of emulsifiers;

Homogenization of milk and similar products;

Cooking/heating of food by introduction of focused sonic energy into the food, either by a purely "sonic" oven, or used in conjunction with other forms of cooking, including microwave and convection ovens;

Disruption of tissue and other material such as breakage of kidney stones or disintegration of cancer cells or tumors;

Cauterization of ruptured blood vessels or body ducts;

Disintegration or dissolution of materials in order to unclog arteries and the like;

Heating cancerous growths so that ionizing radiation treatment will be made more effective;

Facilitating healing by relatively low-intensity sonic application;

Disintegration of blood clots and respiratory congestions; and,

Imaging of structures immersed and/or imbedded within the standing wave medium;

Enhancement of liposuction by sonic breakdown of the fat, allowing the connective tissue to remain in place. With this method, fat may be eliminated by sonic disintegration alone, allowing the body to dispose of the fat that has been freed from the cellular structure. This would eliminate the potential for infection due to penetration of the skin.

The invention disclosed hereinabove employs a plurality of otherwise benign standing waves 18 within a patient's body member 20 to constructively intersect within a target volume 30 of tissue. It will be understood from the foregoing that in the preferred embodiment of the invention the standing waves 18 are produced by opposing pairs of vibrating transducers 10a and 10b. Prior methods and apparatus for generating standing waves in media typically employ a single vibrator mechanism which imparts a coherent vibration into a medium. The wave thus produced propagates through the medium until it encounters a substantially stationary surface off of which the wave bounces directly toward its source. A standing wave may be produced in this manner by adjusting the distance between the vibration source and the reflective surface to an integer multiple of the wavelength of the vibration.

In the preferred embodiment of the present invention, however, standing waves 18 are produced in the medium (i.e. within the body member 20), by a pair of facing transducers working in concert with each other, rather than by a single transducer and a reflective surface. It will be understood that by using a pair of facing transducers working in concert it is possible to precisely vary either the frequency or amplitude or phase relationship of the produced vibrations, or the distance L2 between the facing transducers, in order to set up a standing wave in the patient's body member 20.

It will be understood from the above disclosure that the preferred embodiment of the present invention may be practiced by causing the antinodes of a plurality of intersecting standing pressure waves to constructively interfere with each other at the common point of intersection 34 of the respective standing pressure waves. The use of standing waves are considered preferable (to non-standing waves) because once an antinode of a standing wave is positioned within the target volume 30, it will maintain that position within the target volume. By positioning a number of different standing waves so that each has an antinode within the target volume, the target volume will incur the combined effect of the maximum vibrational energies of the various standing waves as long as each of the waves remains in place.

A target volume 30 will incur the maximum vibrational energy of a given pressure wave when an antinode of that wave is within the target volume. In order for a target volume 30 to incur the maximum vibrational energy from a plurality of pressure waves, antinodes of each of the respective pressure waves must occur simultaneously within the target volume. This condition is achieved in the preferred embodiment of the invention by establishing a plurality of standing pressure waves, each of which passes through, and has an antinode in, the target volume.

Figure 3:
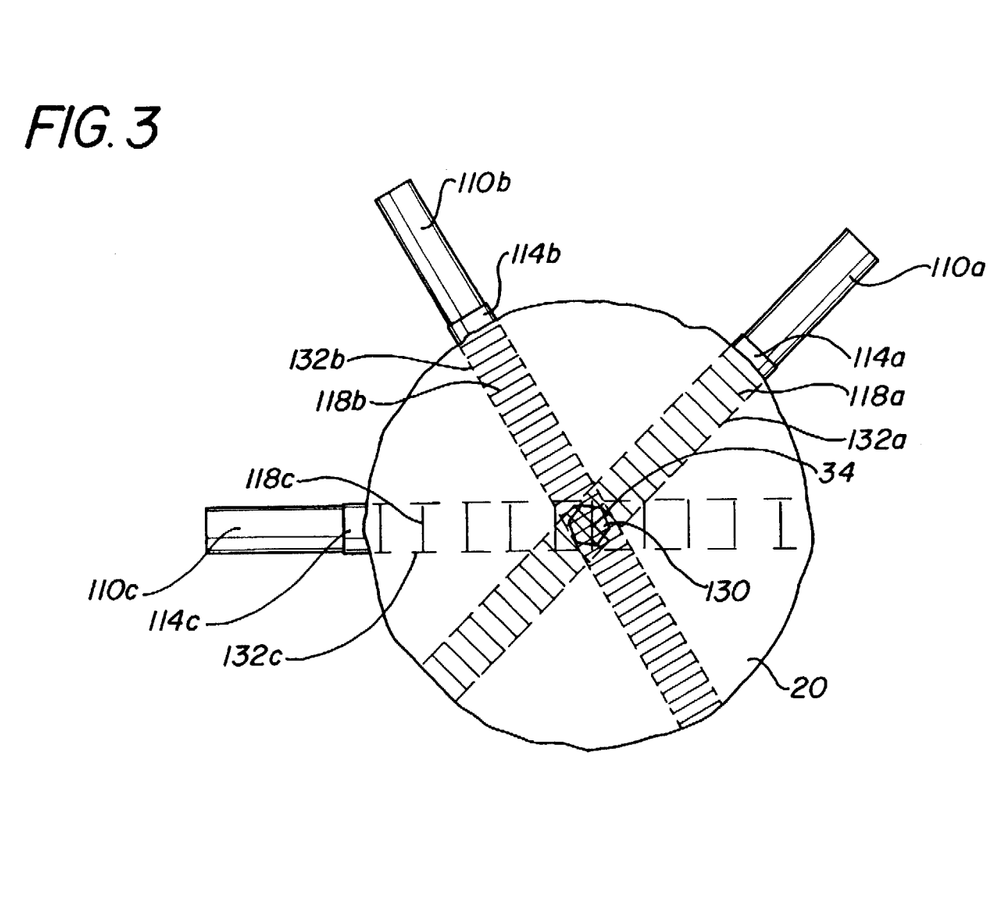
FIG. 3 is a schematic view illustrating a modification of the invention in which a plurality of transducers focus compression waves upon a target volume.
Figure 4:
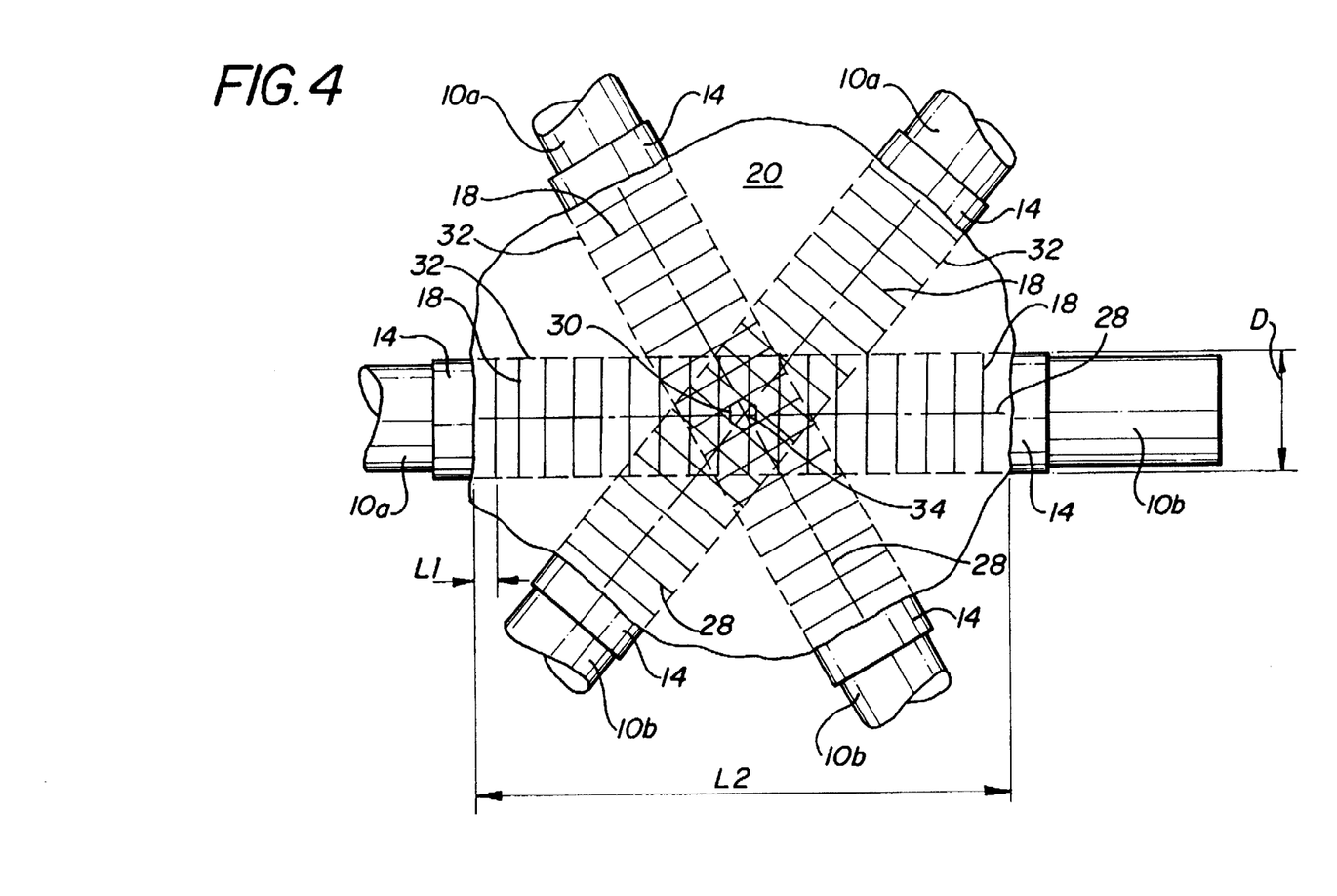
FIG. 4 is a schematic view illustrating a plurality of pairs of opposing transducers used to generate intersecting standing waves within a target volume in accordance with the present invention.

An important modification of the present invention may be practiced by generating a plurality of sonic "beams" (e.g. planar compression waves, each having a wave length which is substantially smaller than the diameter of the vibrating surface 14 from which it propagates) which intersect with each other within the target volume, but do not intersect at a point which continuously corresponds to an antinode of the respective waves. FIG. 3 shows, in cross-section, a patient's body member 20 into which three planar compression waves 118a, 118b and 118c are generated by three transducers 110a, 110b and 110c, respectively, which oscillate three vibrating surfaces 114a, 114b and 114c, respectively. The three planar compression waves 118a, 118b and 118c are in the form of substantially cylindrical "sound beams" generally defined by cylindrical spaces 132a, 132b and 132c, respectively, but which are not necessarily standing waves, and which are not necessarily of identical frequencies. The three waves 118a, 118b and 118c intersect 34 within a target volume 130 which corresponds to the intersection of cylindrical spaces 132a, 132b and 132c. Because the three waves 118a, 118b and 118c are not necessarily standing nor necessarily at the same frequency, their respective antinodes will not occur at the point of intersection 34 within the target volume continuously nor necessarily simultaneously. However, it will be understood that if the three waves 118a, 118b and 118c are of different frequencies (or of similar frequencies whose phase angles are periodically varied), over an extended period of time the antinodes of the three waves 118a, 118b and 118c will occasionally coincide (or nearly coincide) at the point of intersection 34 of the waves within the target volume 130. Whenever the antinodes of the three waves 118a, 118b and 118c occur simultaneously at the point of intersection 34, the target volume 130 will incur vibrational energy whose amplitude far exceeds that experienced at any time within the patient's body 20 outside of the target volume 130. Accordingly, it will be understood that by focusing a plurality of substantially cylindrical planar compression waves upon a target volume (whose lengths along corresponding wave axes is ½ wavelength, or ±¼ wavelength from the point of intersection of the plurality of wave axes) the maximum amplitude of vibration realized within the target volume will far exceed the maximum amplitude of any of the individual compression waves.

For clarity, the examples of the present invention explained above and illustrated in the figures describe embodiments of the invention in which a plurality of transducers are arranged in a single plane about a target volume (i.e. illustrated in the drawings with each transducer being in the plane of the drawing surface). However, the present invention contemplates three-dimensional as well as two-dimensional arrays of transducers.

As discussed above, in the preferred embodiment of the invention the vibrational intensity of interest in the target volume is that which develops transient cavitation within the target volume. However, it is understood that vibrational energy sufficient to cause either thermal, mechanical or cavitional effects within the target volume are all within the scope of the present invention.

While the above description contains many specificities, these should not be construed as limitations on the scope of the invention, but rather as an exemplification of one preferred embodiment thereof. Many other variations are possible, for example:

The frequency of the standing waves 18 generated may either be either in the "sonic" or "ultrasonic" range;

In any given transducer pair (10a and 10b), the amplitudes of the waves generated by opposing vibrating surfaces 14 may be unequal;

Although longitudinal, plane waves are preferred, spherically propagating vibrational waves may alternatively be used;

The present invention may be used to affect target volumes within organic and inorganic media; accordingly the vibration medium need not be a human or animal body member, but may alternatively be any other medium which can sustain a standing wave;

Similarly, the target volume may be organic or inorganic, and, therefore, need not necessarily comprise organic tissue;

Standing waves generated by separate transducer pairs may be of disparate frequencies and/or amplitudes, provided that the antinodes of the standing waves generated by the various transducer pairs occur within the target volume; and The vibrating surface 14 may be an intrinsic component of the transducer 10 member, or the vibrating surface 14 may alternatively comprise a discrete member attached to the transducer;

The standing waves may be generated in a solid or liquid or gas medium, and the medium may be stationary or moving relative to the transducers; in particular the present invention may be practiced upon a moving liquid (for example blood flowing within a stationary body or blood flowing through stationary tubing); and, The vibrating surface 14 may comprise a flat plate which is either circular or non-circular; and The vibrating surface 14 may alternatively be a non-planar surface, including parabolic.

Accordingly, the scope of the invention should be determined not by the embodiment illustrated, but by the appended claims and their legal equivalents.

I claim:

1. A method of applying high intensity vibrational energy to a target volume disposed within a contiguous surrounding medium, comprising the steps of:

introducing vibrational energy into a medium from a first actuator member;

introducing vibrational energy into said medium from a second actuator member;

establishing a first standing pressure wave within said medium between said first actuator member and said second actuator member, said first standing pressure wave having a first longitudinal axis extending through said first actuator member and said second actuator member;

directing said first standing pressure wave through a target volume, said target volume being disposed within said medium and being contiguous with said medium;

positioning an antinode of said first standing pressure wave within said target volume;

introducing vibrational energy into said medium from a third actuator member; introducing vibrational energy into said medium from a fourth actuator member;

establishing a second standing pressure wave within said medium between said third actuator member and said fourth actuator member, said second standing pressure wave having a second longitudinal axis extending through said third actuator member and said fourth actuator member;

directing said second standing pressure wave through said target volume;

positioning an antinode of said second standing pressure wave within said target volume;

wherein said step of introducing vibrational energy into said medium from a first actuator member comprises oscillating a first surface of said first actuator member in a direction parallel to said first longitudinal axis;

wherein said step of introducing vibrational energy into said medium from a second actuator member comprises oscillating a second surface of said second actuator member in a direction parallel to said first longitudinal axis;

wherein said step of introducing vibrational energy into said medium from a third actuator member comprises oscillating a third surface of said third actuator member in a direction parallel to said second longitudinal axis;

wherein said step of introducing vibrational energy into said medium from a fourth actuator member comprises oscillating a fourth surface of said fourth actuator member in a direction parallel to said second longitudinal axis;

wherein said first surface, said second surface, said third surface and said fourth surface are each in contact with said medium;

wherein said first surface and said second surface are each oscillated at a first frequency;

wherein said third surface and said fourth surface are each oscillated at a second frequency;

wherein said step of establishing a first standing pressure wave within said medium between said first actuator member and said second actuator member further comprises generating a first wave length of said first standing pressure wave in said medium adjacent to said first surface, said first wave length being shorter than a first distance measurable across said first surface;

wherein said step of establishing a first standing pressure wave within said medium between said first actuator member and said second actuator member further comprises generating a second wave length of said first standing pressure wave in said medium adjacent to said second surface, said second wave length being shorter than a second distance measurable across said second surface;

wherein said step of establishing a second standing pressure wave within said medium between said third actuator member and said fourth actuator member further comprises generating a third wave length of said second standing pressure wave in said medium adjacent to said third surface, said third wave length being shorter than a third distance measurable across said third surface;

and wherein said step of establishing a second standing pressure wave within said medium between said third actuator member and said fourth actuator member further comprises generating a fourth wave length of said second standing pressure wave in said medium adjacent to said fourth surface, said fourth wave length being shorter than a fourth distance measurable across said fourth surface.

2. The method according to claim 1, wherein said step of directing said first standing pressure wave through said target volume comprises positioning said first longitudinal axis to pass through said target volume;

and wherein said step of directing said second standing pressure wave through said target volume comprises positioning said second longitudinal axis to intersect with first longitudinal axis within said target volume.

3. The method according to claim 2, wherein said first standing pressure wave and said second standing pressure wave constructively interfere with each other within said target volume.

4. The method according to claim 3, wherein said first frequency and said second frequency are equal.

5. A method of applying high intensity vibrational energy to a target volume disposed within a contiguous surrounding medium, comprising the steps of: introducing vibrational energy into a medium from a first actuator member;

introducing vibrational energy into said medium from a second actuator member;

establishing a first standing planar wave within said medium between said first actuator member and said second actuator member, said first standing planar wave having a first longitudinal axis extending through said first actuator member and said second actuator member;

directing said first standing planar wave through a target volume, said target volume being disposed within said medium and being contiguous with said medium;

positioning an antinode of said first standing planar wave within said target volume;

wherein said step of introducing vibrational energy into said medium from a first actuator member comprises oscillating a first planar surface of said first actuator member in a direction parallel to said first longitudinal axis;

wherein said step of introducing vibrational energy into said medium from a second actuator member comprises oscillating a second planar surface of said second actuator member in a direction parallel to said first longitudinal axis;

wherein said first planar surface and said second planar surface are each in contact with said medium;

wherein said first planar surface and said second planar surface are each oscillated at a first frequency;

wherein said step of establishing a first standing planar wave within said medium between said first actuator member and said second actuator member further comprises generating a first wave length of said first standing planar wave in said medium adjacent to said first planar surface, said first wave length being shorter than a first distance measurable across said first planar surface;

wherein said step of establishing a first standing planar wave within said medium between said first actuator member and said second actuator member further comprises generating a second wave length of said first standing planar wave in said medium adjacent to said second planar surface, said second wave length being shorter than a second distance measurable across said second planar surface.

6. The method according to claim 5, wherein said step of directing said first standing planar wave through said target volume comprises positioning said first longitudinal axis to pass through said target volume.

7. The method according to claim 5, wherein said first planar surface reflects said first standing planar wave at said first frequency;

and wherein said second planar surface reflects said first standing planar wave at said first frequency.

8. The method according to claim 7, wherein said first standing planar wave extends from said first planar surface to said second planar surface.

9. The method according to claim 8, further comprising the steps of:

introducing vibrational energy into said medium from a third actuator member;

introducing vibrational energy into said medium from a fourth actuator member;

establishing a second standing planar wave within said medium between said third actuator member and said fourth actuator member, said second standing planar wave having a second longitudinal axis extending through said third actuator member and said fourth actuator member;

directing said second standing planar wave through said target volume;

positioning an antinode of said second standing planar wave within said target volume;

wherein said step of introducing vibrational energy into said medium from a third actuator member comprises oscillating a third planar surface of said third actuator member in a direction parallel to said second longitudinal axis;

wherein said step of introducing vibrational energy into said medium from a fourth actuator member comprises oscillating a fourth planar surface of said fourth actuator member in a direction parallel to said second longitudinal axis;

wherein said third planar surface and said fourth planar surface are each in contact with said medium;

wherein said third planar surface and said fourth planar surface are each oscillated at a second frequency;

wherein said step of establishing a second standing planar wave within said medium between said third actuator member and said fourth actuator member further comprises generating a third wave length of said second standing planar wave in said medium adjacent to said third planar surface, said third wave length being shorter than a third distance measurable across said third planar surface;

and wherein said step of establishing a second standing planar wave within said medium between said third actuator member and said fourth actuator member further comprises generating a fourth wave length of said second standing planar wave in said medium adjacent to said fourth planar surface, said fourth wave length being shorter than a fourth distance measurable across said fourth planar surface.

10. The method according to claim 9, wherein said step of directing said second standing planar wave through said target volume comprises positioning said second longitudinal axis to intersect with first longitudinal axis within said target volume.

11. The method according to claim 10, wherein said first standing planar wave and said second standing planar wave constructively interfere with each other within said target volume.

12. The method according to claim 11, wherein said third planar surface reflects said second standing planar wave at said second frequency;

and wherein said fourth planar surface reflects said second standing planar wave at said second frequency.

13. The method according to claim 12, wherein said second standing planar wave extends between said third planar surface and said fourth planar surface.

* * * * *